(12) United States Patent
Hunter (10) Patent No.: US 6,309,600 B1
(45) Date of Patent: Oct. 30, 2001

(54) APPARATUS FOR DROPLET MICROCHEMISTRY (75) Inventor: Ian W. Hunter, Lincoln, MA (US)

(73) Assignee: BioTrove, Inc., Cambridge, MA (US)

( * ) Notice: Subject to any disclaimer, the term of this patent is extended or adjusted under 35 U.S.C. 154(b) by 0 days.

(21) Appl. No.: 09/081,700

(22) Filed: May 20, 1998

Related U.S. Application Data (60) Provisional application No. 60/057,734, filed on Aug. 28, 1997.

(51) Int. Cl.$^7$ .................................................... G01N 35/10
(52) U.S. Cl. ........................................... 422/66; 422/100
(58) Field of Search ............................... 422/63, 66, 100, 422/103; 436/43, 44, 174, 180

(56) References Cited

U.S. PATENT DOCUMENTS

| | | | |
|---|---|---|---|
| 3,566,677 | 3/1971 | Cole et al. | 73/61.3 |
| 3,710,279 | 1/1973 | Ashkin | 331/94.5 |
| 3,734,622 | 5/1973 | Adler | 356/103 |
| 3,855,846 | 12/1974 | Forget et al. | 73/61.1 |
| 3,929,004 | * 12/1975 | Gunew et al. | 73/61.1 C |
| 4,055,987 | * 11/1977 | McFadden | 73/61.1 C |
| 4,071,315 | 1/1978 | Chateau | 23/230 B |
| 4,111,553 | 9/1978 | Garnys | 356/36 |
| 4,113,383 | * 9/1978 | Burns et al. | 356/36 |
| 4,196,615 | 4/1980 | Davis | 73/64.4 |
| 4,568,875 | 2/1986 | Piso et al. | 324/61 R |
| 4,659,677 | 4/1987 | Glover et al. | 436/174 |
| 4,837,160 | 6/1989 | Meserol et al. | 436/45 |
| 4,841,145 | 6/1989 | Wada et al. | 250/304 |
| 4,883,642 | 11/1989 | Bisconte | 422/102 |
| 5,006,749 | 4/1991 | White | 310/323 |
| 5,122,284 | 6/1992 | Braynin et al. | 210/782 |
| 5,334,837 | 8/1994 | Ikeda et al. | 250/339 |
| 5,486,337 | 1/1996 | Ohkawa | 422/100 |
| 5,516,692 | 5/1996 | Berndt | 435/286.7 |
| 5,643,628 | 7/1997 | Sonderegger | 427/231 |

FOREIGN PATENT DOCUMENTS

| | | |
|---|---|---|
| 247 857 A1 | 7/1987 | (DE) . |
| 2307075 | 8/1974 | (EP) . |
| 0 286 419 A2 | 10/1988 | (EP) . |
| 93102257.8 | 2/1993 | (EP) . |
| 0 641 599 A1 | 3/1995 | (EP) . |
| 0752 281 A2 | 1/1997 | (EP) . |
| 60022478 | 2/1985 | (JP) . |
| 8-334455 | 12/1996 | (JP) . |
| WO 83/03677 | 10/1983 | (WO) . |
| WO 91/16966 | 11/1991 | (WO) . |
| WO 95/34374 | 12/1995 | (WO) . |
| WO 98/08093 | 2/1998 | (WO) . |
| WO 98/15355 | 4/1998 | (WO) . |

* cited by examiner

Primary Examiner—Jeffrey Snay
(74) Attorney, Agent, or Firm—Bromberg & Sunstein LLP (57) ABSTRACT An apparatus and methods for performing microchemical manipulation and analysis of liquid samples. One or more droplets of liquid are loaded serially or in parallel onto a flexible member which may be a fiber or a tape, and are retained on the flexible member by virtue of surface adhesion. Microchemical operations may be performed on these droplets, the operations including mixing, dilution, concentration, heating, cooling, filtering, and analyzing, where the analyzing may include chemical, biochemical, optical, or other physical analyses.

10 Claims, 9 Drawing Sheets

APPARATUS FOR DROPLET MICROCHEMISTRY

This application claims benefit of U.S. provisional application No. 60/057,734, filed Aug. 28, 1997, which is herein incorporated by reference.

TECHNICAL FIELD

The present invention pertains to an apparatus and methods for transporting a massive number of droplets of liquid and for performing microchemical operations on these droplets, the operations including mixing, dilution, concentration, heating, cooling, filtering, and analyzing, where the analyzing may include chemical, biochemical, optical, or other physical analyses.

BACKGROUND OF THE INVENTION

Chemistry on the micro-scale, involving the reaction and subsequent analysis of quantities of reagents or analytes of order microliters or smaller, is an increasingly important aspect of the development of new substances in the pharmaceutical and other industries (e.g., synthesis and analysis of new conductive polymers, phosphors, superconductors, etc.). Such reaction and analysis must accommodate vast libraries of compounds to be reacted and analyzed under various conditions. Significant problems associated with current technologies as applied to chemical analysis of vast numbers (potentially on the order of hundreds of thousands or millions per day) of compounds include the problem of conveying analytes from well plates in which libraries of compounds are kept to regions of reaction and analysis, potential contamination of the transport medium, and the sheer size of the facility required to handle vast numbers of compounds and reactions.

Existing technology applies 96-well plates containing quantities on the order of 1 milliliter of liquid compound per well, and, generally, envisions chemical reactions and analysis on flat, two-dimensional surfaces such as silicon chips. In addition to the parallel processing of liquid samples provided by chip technology, a method is required to perform serial steps of liquid sampling, transport, and microchemical analysis.

SUMMARY OF THE INVENTION

In accordance with a preferred embodiment of the invention, there is provided an apparatus for transporting one or more droplets of a liquid. The apparatus has a reservoir for containing a quantity of the liquid and a flexible member for receiving the droplet or droplets of liquid from the reservoir, with the droplets adhering to the flexible member by virtue of the surface adhesion of the liquid. The flexible member may be a fiber or a ribbon, and a portion of the flexible member may be formed at least temporarily into an enclosure for encapsulating at least one droplet of the liquid.

In accordance with a preferred embodiment of another aspect of the present invention, there is provided an apparatus for storing or analyzing a plurality of liquid droplets. The apparatus has a drum having a substantially cylindrical surface and a plurality of wells disposed within the substantially cylindrical surface. The apparatus also has a dispenser for injecting the plurality of droplets into the wells according to a predetermined schedule and may have an analyzer for characterizing at least one chemical property of the droplets. The dispenser may be a flexible transport member wrapped onto the drum in such a manner as to position no more than one droplet of liquid in each well of the drum.

In accordance with other aspects of the present invention, methods are provided for transporting, sampling, mixing, concentrating, diluting, heating, cooling, and analyzing liquid samples by extracting a volume of the liquid by means of the apparatus discussed above. Analysis of physical and chemical properties of the samples may be performed in series or in substantial parallelism.

BRIEF DESCRIPTION OF THE DRAWINGS

The invention will be more readily understood by reference to the following description, taken with the accompanying drawings, in which.

DETAILED DESCRIPTION OF PREFERRED EMBODIMENTS

Figure 1A:
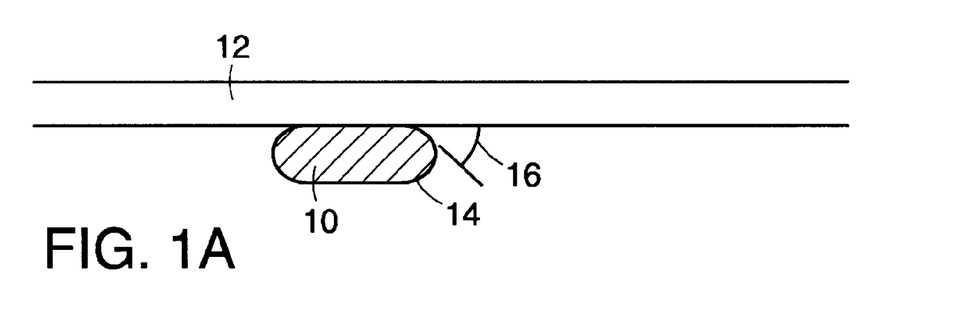
FIGS. 1A–1C are side views in cross-section of a droplet in adhesion to a fiber in accordance with an embodiment of the present invention.

Referring first to FIG. 1A, it is recognized that transport, manipulation, and microchemical reaction of materials in the liquid phase or in liquid suspension need not be conducted in a planar environment but may use the adhesion of a droplet 10 to a fiber 12 in order to achieve one or more of the enumerated processes. Processes of adhesion of a liquid to the surface of a solid are discussed, for example, in D.

Myers, *Surfaces, Interfaces, and Colloids: Principles and Applications*, (VCH Publishing, N.Y. 1991), which is incorporated herein by reference. Chapter 17, entitled "Wetting and Spreading," at pp. 349ff, is of particular relevance.

"Fiber," as used in the present description and in any appended claims, refers to any flexible material the linear dimension of which substantially exceeds the transverse dimensions of the material and includes materials which may be amorphous, such as glass or plastic. It is the geometry rather than the composition of the fiber which is germane to the overall scope of the invention, although the properties of different compositions of fiber may be advantageously exploited, as further described below. The transverse section of the fiber may have any specified shape, thus the fiber may be of circular or elliptical cross section, in the manner of optical fibers, for example. The flexible member may also be flat and ribbon-like, or curled, as discussed below, and references herein to "fiber" are to be understood as also encompassing the generality of flexible members. Materials may include quartz or glass, for example, or amorphous metal (metallic glass), as another example. Metal wires of diameters as small as 25 μm, or even 5 μm, are readily available. Droplet 10 may be referred to herein and in the appended claims as a "microdroplet" or a "sample," and may include droplets containing living cells, such as yeast cells, for example and may include droplets carrying a single living cell per droplet.

The fiber system described herein for droplet microchemistry may entirely avoid the use of tubes which require cleaning, and may overcome various handling difficulties associated with samples enclosed in conduits. By way of contrast, glass fibers are available at low cost in lengths as long as many kilometers and are readily disposed of after chemical manipulation and analysis are completed.

The following components of a microchemical analysis system are examples of processes which may be carried out through the use of fiber technology in accordance with various embodiments of the present invention:

1. Sampling—i.e., transferring a small amount of a specified fluid to a fiber from either a reservoir of fluid or another surface;
2. Transporting fluid samples;
3. Adding one sample to another;
4. Diluting a sample;
5. Concentrating a sample;
6. Heating or Cooling a sample;
7. Extracting or filtering chemicals contained within a sample;
8. Analyzing chemicals as to their composition or other chemical or physical characteristics.

Figure 1B:
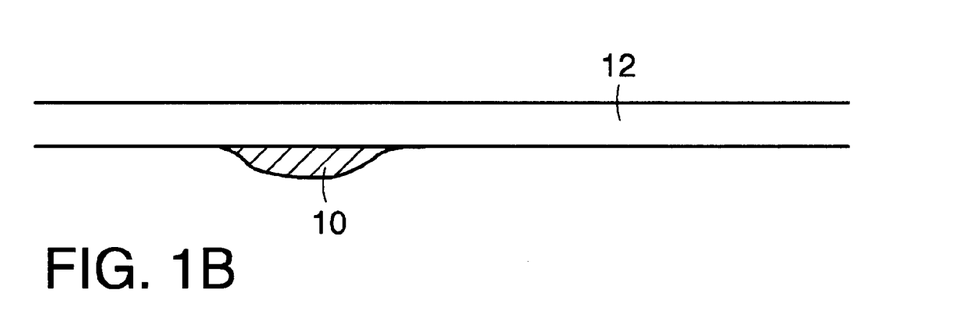

The quantity of fluid adhering to fiber 12 and thus constituting droplet 10 is a function of the respective compositions of fiber 12 and droplet 10 and of the method in which adhesion of the droplet to the fiber is attained. In practice, variations in volume of over a factor of 1000 have been achieved. The surface tension of droplet 10, for example, serves to counter unlimited diffusion of the fluid along the length of the fiber. Where fiber 12 is not wetted by droplet 10, tangent 16 to outer surface 14 of droplet 10 forms contact angle 18 with the local surface of fiber 12. Where wetting of fiber 12 by droplet 10 occurs, as shown in FIG. 1B, the spread of droplet 10 along fiber 12 is limited by surface tension. The size of the droplet is related to the transverse dimension (or dimensions) of the fiber; for example, a fiber of 100 μm diameter may hold a droplet of over five times that diameter.

Figure 1C:
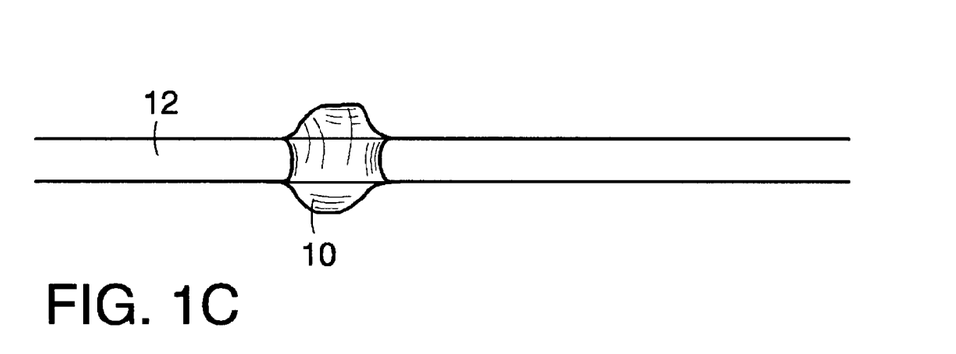

For transportation of droplet 10, it is preferred that droplet 10 surround fiber 12, as shown in FIG. 1C.

Sampling of materials in liquid form, thereby loading the fiber, is now described with reference to FIG. 2. Fiber 12 may be guided, by any mechanical arrangement known in the mechanical arts, so as to come in contact with liquid 18 which may be contained within reservoir 20. Quartz is a preferred material for fiber 12 as it is very strong. Fiber 12 may be guided, for example, by means of pulleys 22, comprising pulley feed mechanism 23, so as to form loop 24. Loop 24 is brought in a direction designated by arrow 26 into contact with liquid 18, as shown in FIG. 2B, preferably without penetrating the surface of the liquid. As loop 24 is withdrawn in direction 28 away from the surface of the liquid, as shown in FIG. 2C, droplet 10 begins to form on fiber 12. As loop 24 is withdrawn further, droplet 10 detaches from liquid reservoir 20, as shown in FIG. 2D.

The rate at which fiber 12 is withdrawn from liquid reservoir 20 contributes to determining the size of droplet 10 that is formed, with a slower withdrawal resulting in a smaller droplet. Higher velocities result in larger droplets, whereas higher velocities yet result in loss of the droplet to dripping back into the reservoir. Pulley feed mechanism 23 also serves to impel fiber 12 in the direction of its longitudinal axis.

A typical volume of fluid sampled by a fiber in the manner described is of the following order: assuming a sphere of fluid having a diameter of 300 μm surrounding a fiber of 100 μm diameter, and removing the volume displaced by the presence of the fiber, the volume of the liquid droplet is on the order of 12 nanoliters. Since the volume of the droplet scales substantially as the cube of the characteristic transverse dimension of the fiber, a fiber of 1 mm diameter may be used to transport droplets of volume on the order of 10 microliters. In fact, droplet volumes between 10 picoliters and 10 microliters are readily handled in accordance with the invention.

Figure 2A:
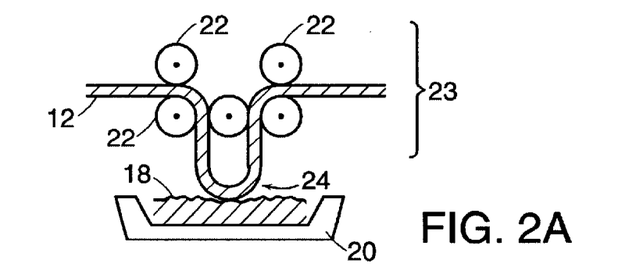
FIG. 2A is a side view in cross section of a liquid take-up mechanism in accordance with an embodiment of the present invention.
Figure 2B:
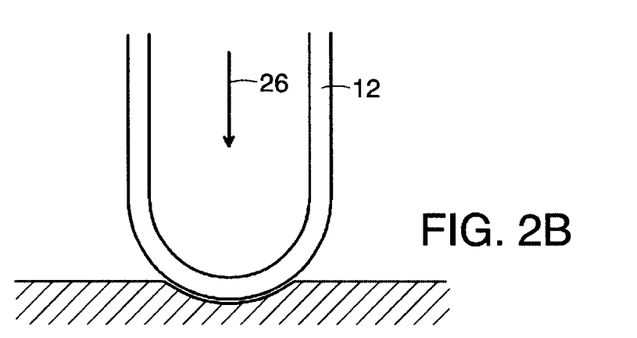
FIGS. 2B–2D show successive steps of liquid take-up onto a fiber in accordance with the embodiment of FIG. 2A.
Figure 2C:
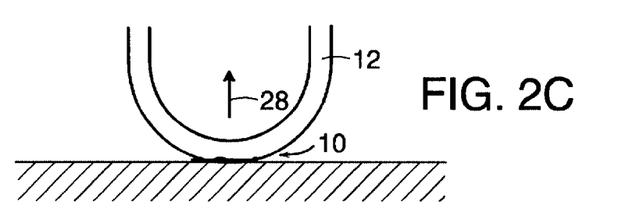
Figure 2D:
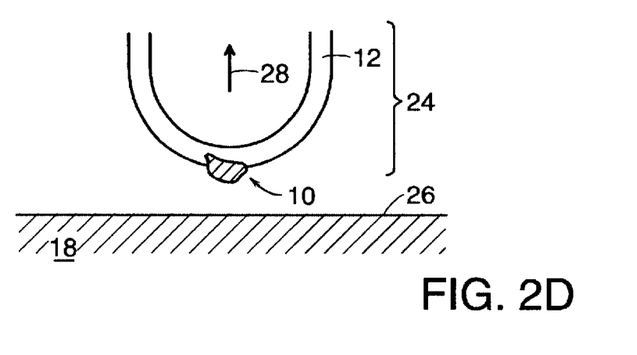

Referring, once more, to FIG. 2A, contact between fiber 12 and the liquid in reservoir 20 may be achieved in any of a variety of ways. In accordance with a preferred embodiment of the invention, reservoir 20 may be raised so that surface 26 of liquid 18 makes contact with fiber loop 24.Alternatively, the entire pulley feed mechanism 23 may be lowered to that loop 24 makes contact with liquid 18, or, in accordance with another embodiment, the speed of rotation of pulleys 22 may be differentially governed to regulate the length of loop 24. It is to be understood that additional pulleys may be provided within the scope of the invention, such as to provide for differential advancement of the leading and trailing knees of loop 24.

Transportation

Figure 3:
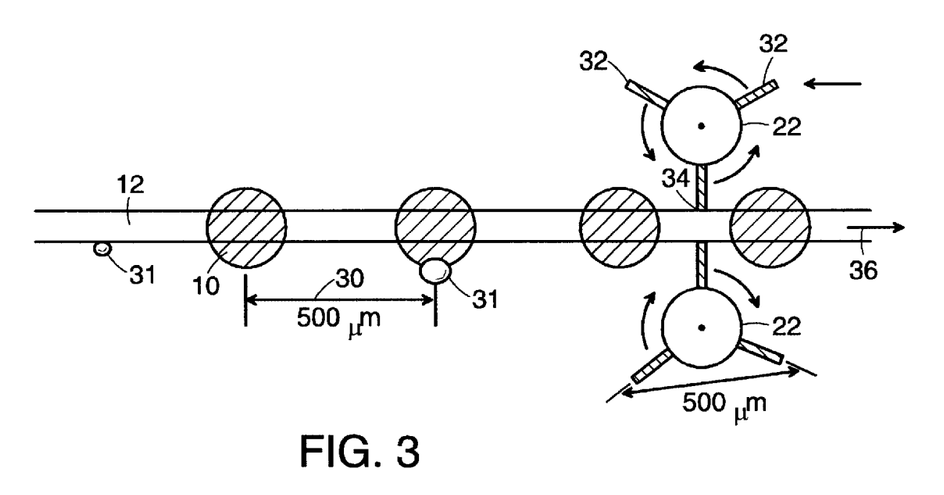
FIG. 3 depicts the transport of multiple droplets on a fiber, and an advancement mechanism for translating the fiber in accordance with an embodiment of the invention.

A fiber, as described, may hold a large number of liquid droplets and convey all the droplets in a specified direction for serial handling on a massive scale. Referring now to FIG. 3 and considering fiber 12 to have a diameter of 100 μm, for example, droplets 10 may be conveyed with an inter-droplet spacing 30 of 500 μm or less. Thus, over 2000 droplets may be loaded per meter of fiber, and 500 m of fiber can hold and transport over one million droplets, where the composition of the individual droplets may vary.

Additionally, in accordance with a further embodiment of the invention, small solid particles 31 may be held to fiber 12 by electrostatic attraction or by forces of liquid surface adhesion and similarly transported, manipulated and analyzed by the disclosed system. In order for fiber 12 to be advanced by pulleys 22, provision must be made not to interfere with the conveyance of droplets 10. One method of providing for fiber advancement is to provide radial members 32 that contact fiber 12 only at positions 34 where no droplets are present. Pulleys 22 are shown in this figure to be counterrotating so as to advance fiber 12 in direction 36, to the right in this figure.

In an alternate embodiment of the invention, the fiber may be magnetized at specified locations or intervals and a magnetically attractable bead may be attracted at those locations and surrounded by the liquid to be transported.

Once droplets 10 have been loaded onto fiber 12, they may be heated or cooled, and functions of microchemistry and analysis may be performed on them, as discussed in greater detail in the following discussion.

Addition of Chemicals Via Fiber Technology

Figure 4:
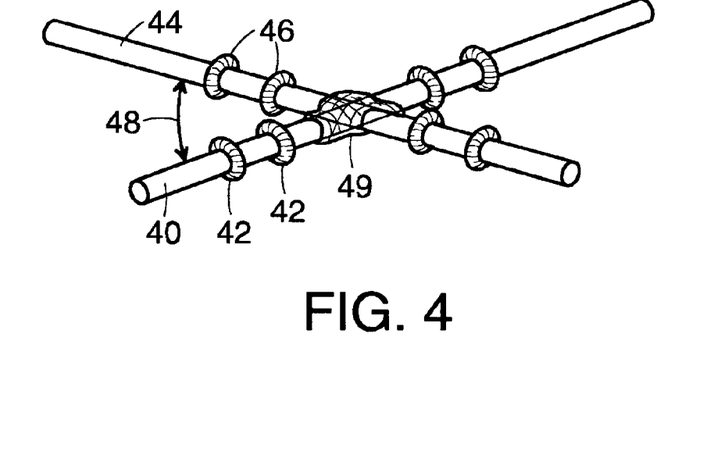
FIG. 4 depicts the combination of droplets transported to the cite of combination by respective fibers in accordance with an embodiment of the present invention.

Referring now to FIG. 4, distinct droplets, of the same or different chemical composition, may be combined using the droplet microchemistry methods of the present invention. A first fiber 40, carrying droplets 42 may be moved with respect to a second fiber 44 carrying other droplets 46 such that fibers 40 and 44 lie in substantially locally parallel planes and have a specified relative angle 48 which may be a right angle. When fiber 40 is brought within sufficient proximity of fiber 44, a single droplet 49 may be formed by the combination of droplets from each of fibers 40 and 44. When fiber 40 is now moved away from fiber 44, combined droplet 49 tends to move to one or the other of fibers 40 and 44. In order to select which fiber will receive combined droplet 49, one fiber, say, for example, fiber 44, may be moved substantially transversely to the other fiber, and then the fibers are separated. The fibers are distinguished in this way since the force required to move a droplet along a fiber differs from the force required to remove the droplet from the fiber or to impart momentum to the liquid in a direction tangential to the circumference of the fiber.

In the manner described, thousands of droplets conveyed by a single fiber may be combined with thousands of droplets conveyed by a second fiber by sequentially bringing the droplets into mutual contact.

Figure 5:
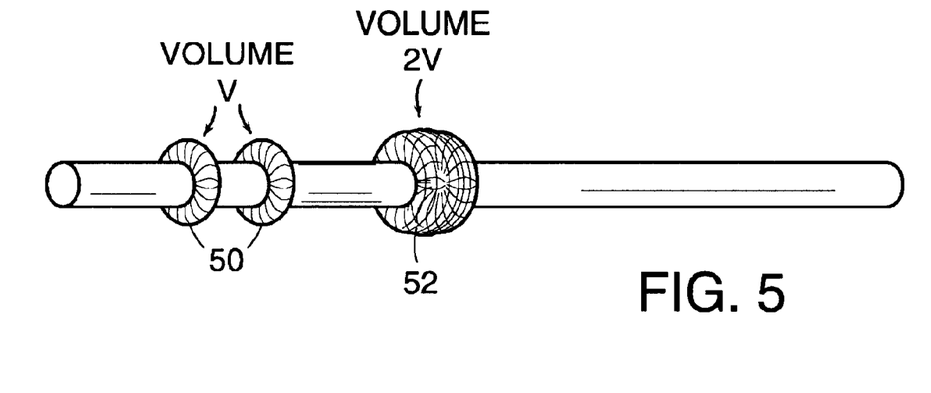
FIG. 5 depicts the respective surface areas and volumes of individual and combined droplets borne by a fiber in accordance with an embodiment of the present invention.

In FIG. 5, the surface areas and volumes of two droplets 50, assumed to be equal, are compared with the same quantities of combined droplet 52 which results from the combination of the original droplets 50 in accordance with the preceding discussion. While the volume of fluid of droplet 52 is twice that of either droplet 50, the surface area of droplet 52 is less than twice that of either droplet 50. Since the surface area of droplet 52, and thus its surface energy which increases with surface area, is less than the sum of the corresponding quantities for the separate droplets, the combination configuration is energetically favored.

Figure 6:
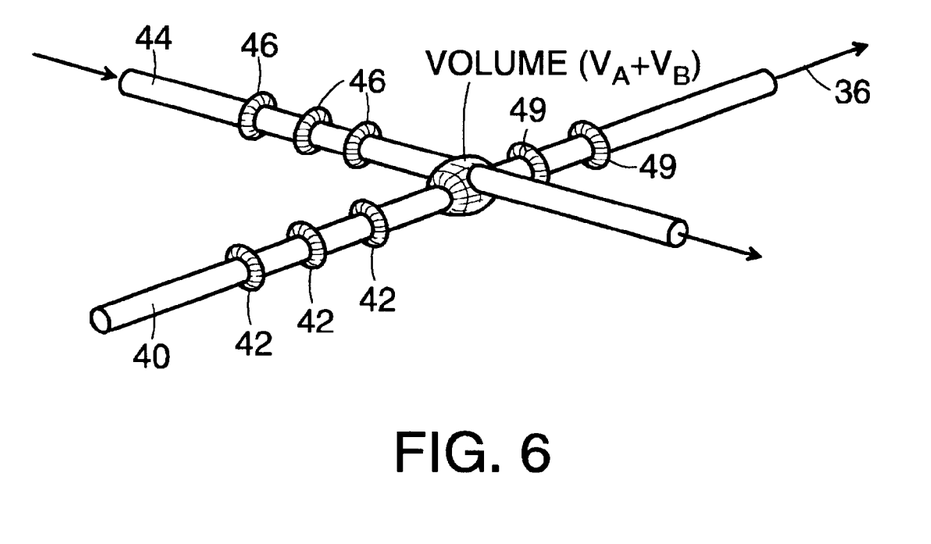
FIG. 6 shows the transport and combination of droplets of varying sizes in accordance with an embodiment of the invention.

As shown in FIG. 6, droplets 42 transported by fiber 40 in axial direction 36 may be of a different size or volume from droplets 46 transported by fiber 44 prior to their combination with droplets 44 to produce combined droplets 49. In fact, within the scope of the invention, there is no restriction on the sizes of particular droplets. Since the chemical composition of the various droplets is controlled, a computer may track them all and control the chemical reactions taking place among the droplets.

Probes of Droplet Position and Physical Characteristics

Capacitive

Figure 7:
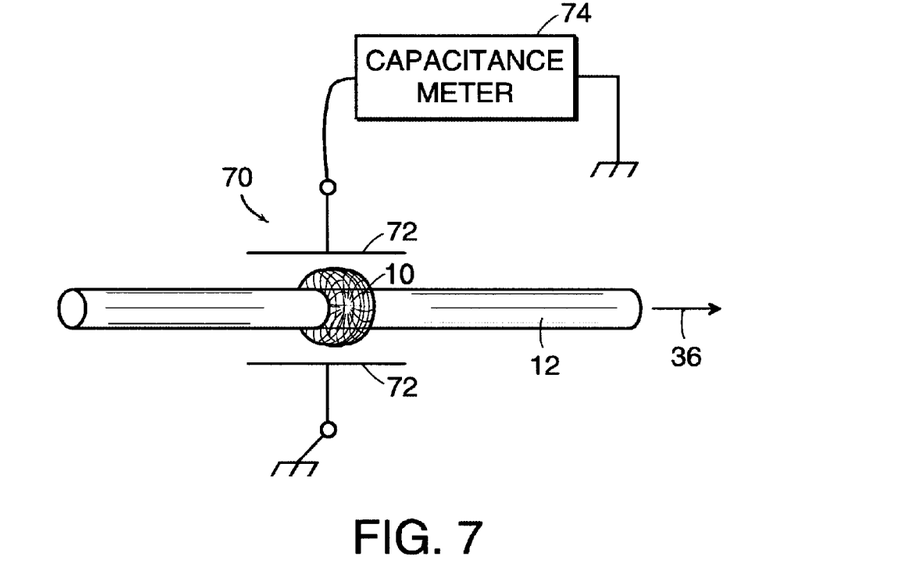
FIG. 7 is a schematic diagram of a capacitive monitor for sensing the position and characteristics of a microdroplet in accordance with an embodiment of the invention.
Figure 8:
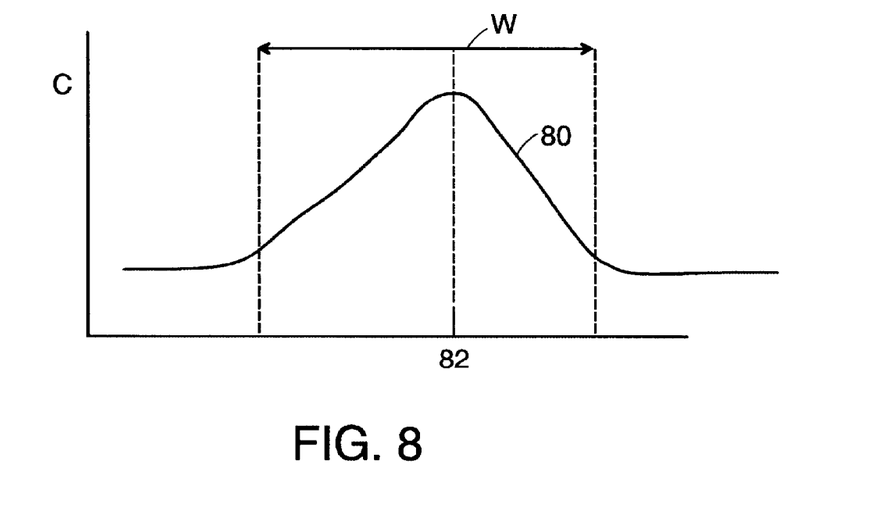
FIG. 8 is a plot of the measured capacitance as a droplet traverses the capacitive monitor of FIG. 7.

Variability in droplet position with reference to laboratory-fixed instrumentation may arise because of lengthening or shortening of the fiber due, in turn, to thermal expansion or tensile stress, for example. In order to track the droplet position with great precision, several methods may be practiced. Referring to FIG. 7, a capacitance sensor, designated generally by numeral 70, is used to measure the capacitance between plates 72. A capacitance meter 74, such as known in the art, is connected across the plates and supplies an output signal characterizing the capacitance. The clearance between plates 72 must be sufficient to provide clearance for fiber 12 and droplet 10, while the width of plates 72 must be no longer than to allow clear resolution of individual droplets. Depending on the dielectric properties of a given droplet 10, the capacitance measured across plates 72 increases or decreases as droplet 10 enters the region between the plates, as fiber 12 advances in direction 36. The plot 80 in FIG. 8 depicts the capacitance, plotted along the vertical axis, as a function of the displacement x of fiber 12. The width w of the capacitance feature corresponds, substantially, to the width of the droplet convolved with the width of plates 72, and may be dominated by the width of the plates if it significantly exceeds the width of the droplet. Using this technique, the mid-droplet position 82 is accurately determined.

Plot 80 of capacitance as a function of fiber position also allows other parameters to be determined. For example, the integral of curve 80 is proportional to the volume of the droplet for a given plate geometry and dielectric constant of the liquid. By making the plate length shorter than the droplet length, the width of the curve yields the droplet length directly, and, otherwise, the droplet width may be derived by deconvolution of the known plate width. Similarly, the dielectric constant of the liquid and the known dielectric properties and geometry of the fiber allow the volume to be derived given an absolute measurement of incremental change in capacitance as the droplet passes through the plates.

Similarly, once the droplet volume and length are known, the diameter is readily calculated.

Alternatively, if the volume of the droplet is derived by independent means such as by one of the optical methods described below, the capacitance technique described may be used to infer the dielectric constant of the droplet and thus aspects of its material/chemical characteristics.

Optical

Figure 9:
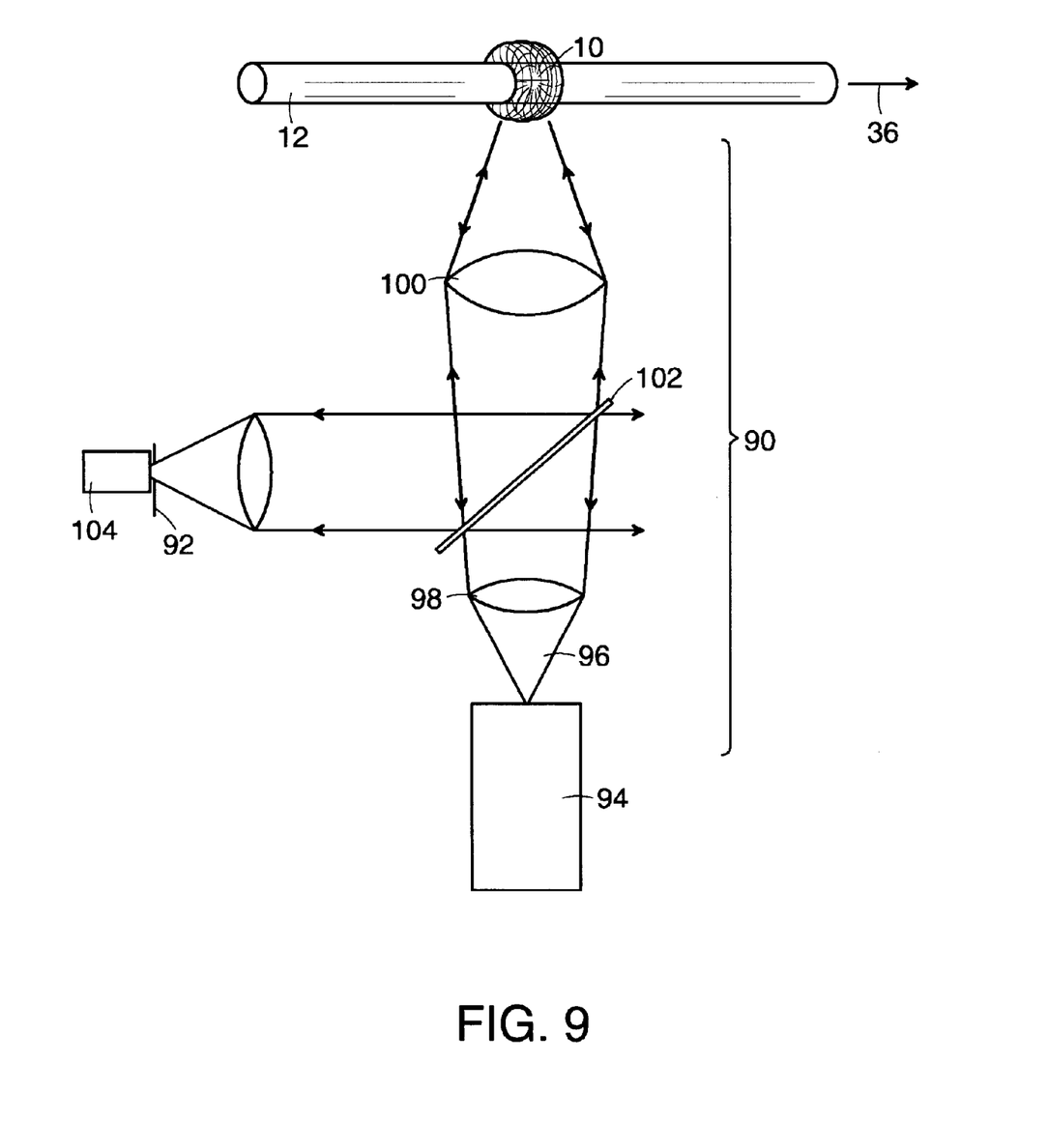
FIG. 9 is a schematic diagram of a typical optical configuration employed for interrogating a droplet in accordance with an embodiment of the present invention.

Referring now to FIG. 9, other methods for interrogating the physical and chemical properties of droplet 10 conveyed in direction 36 by fiber 12 employ a microscope designated generally by numeral 90. The optical arrangement may be confocal (of Type I or Type II) with the interrogated droplet 10 and an aperture stop 92 at conjugate foci of the system, or otherwise, using any optical arrangement known to persons skilled in the optical arts. Using any such arrangement, a source of illumination 94, which may be a broadband source of light or a monochromatic source such as a laser, provides a light beam 96 that is collimated by collimating optics 98. In accordance with a preferred embodiment of the invention, beam 96 is focused by focussing optics 100 to form a focus in the vicinity of droplet 10. A fraction of the light reflected from droplet 10 is deflected by beam-splitter 102 and focussed onto photodetector 104.

As droplet 10 traverses beam 96, the intensity of reflected light measured at photodetector 104 varies, with optimal performance achieved when aperture stop 92 is matched to the size of droplet 10. As discussed above, an optical technique may be employed to derived droplet size, whereupon the capacitive technique yields information relating to the dielectric properties of the individual droplets.

In accordance with further embodiments of the invention, the light returned from the droplet, whether by reflection or scattering, may be spectrally analyzed, using any or all spectroscopic techniques known in the spectroscopic arts, to derive information regarding the composition and physical state of the liquid comprising droplet 10. These techniques include fluorescence detection systems based on the fluorescent response, for example, to target drug/protein interactions.

Additionally, microscope arrangement 90 may be employed to create an image of droplet 10 at the focal plane where aperture stop 92 is shown. Placing a camera array, such as a CCD array, in the focal plane allows an image signal to be derived, according to standard optical techniques.

Longitudinal Propulsion of Droplets Along the Fiber

In addition to conveyance of the droplets by moving the underlying fiber, one or more droplets may be moved relative to the fiber. In accordance with one technique for moving a droplet, optical tweezers are employed, using the known effect of dipole forces created by the scattering of light as it passes through a diffractive interface between two dielectric media such as the ambient air and the droplet. The light beam is applied by focussing a laser beam to a confocal zone of the same dimension as the droplet such that the droplet is constrained to remain within the waist of the beam.

In accordance with an alternate embodiment of the invention, acoustic pulses are launched from opposite ends of the droplet-laden fiber by means of acoustic transducers such as piezo actuators. The two pulses are designed such that they collide to create an asymmetric longitudinal pulse tending to urge the fiber and thus the droplet preferentially in one direction along the axial length of the fiber. This forms a type of "inertial stepping" as is known in the art of tunneling microscopy for moving solid objects. Using this technique, particular droplets along the fiber may be addressed.

Various embodiments of the invention, as described above, may be advantageously employed for sampling droplets from a 96-well plate such as is used extensively in areas of biology, pharmacology, etc. A single fiber may be used for sequentially sampling droplets from each of the 96 wells on the plate. In accordance with an alternative embodiment of the invention, a sampling assembly, such as depicted in FIG. 2A, provides for simultaneous sampling of a plurality of wells by means of a plurality of loops, either of the same fiber or of various fibers. This provides for rapid sampling and conveyance of large numbers of microdroplets, of as many as 96,000 droplets sampled from 1000 plates in the course of on the order of 1.5 hours.

Fiber Storage and Analysis

Figure 10:
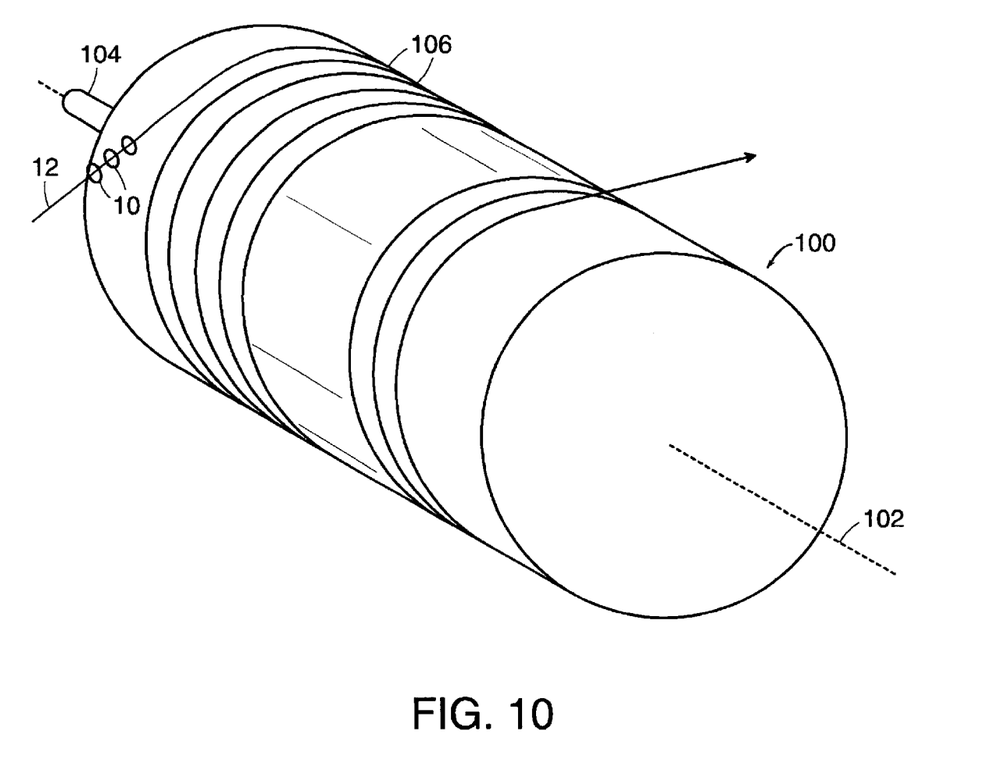
FIG. 10 is a perspective view of a sample handling drum for storage and analysis of microsamples conveyed by fiber in accordance with embodiments of the invention.

Referring now to FIG. 10, a retaining drum 100 is shown which may serve one or more of the following three functions: a) retaining the droplet-laden fiber 12 in such a manner as not to perturb the integrity of the droplets; b) pulling fiber 12 for conveyance of droplets 10 suspended therefrom; and c) providing a platform for analysis, in massive parallelism if required, of suspended droplets 10.

Drum 100 is rotated about its axis 102 by means of a motor (not shown) driving shaft 104, via any appropriate mechanical coupling. Drum retains fiber 12 in spiral groove 106 which has a pitch equal to the fiber turn-to-turn spacing when the fiber is wound on the drum. Fiber 12 may be taken up or unwound from either end, as shown. In a preferred embodiment, fiber 12 is continuously taken up and paid out, possibly to a further drum for subsequent analysis or to a spool for disposal. A typical pitch may be 500 $\mu$m. For an interdroplet spacing of 500 $\mu$m, a drum of 100-mm circumference holds 200 samples per revolution, and, with a 500$\mu$m pitch, $10^5$ samples per 250-mm length of drum may be retained for storage or analysis. Groove 106 has indentations, holes, or depressions (wells) at the droplet spacing so that the droplets are not perturbed by winding of fiber 12 on drum 100. These holes may be employed for optical transmission between the interior and exterior of the drum to facilitate optical analysis by means of a detector addressing individual droplets, serially or in parallel by means of a detector array. In a preferred embodiment, a stepping motor is employed for rotating the drum, the motor having 100,000 steps per revolution for accurate registration of the drum position. Such a motor provides 1-$\mu$m positioning capability with respect to the fiber wound on the drum.

It is to be understood that samples 10 may either be retained in adhesion to fiber 12 while wound on drum 100, or, alternatively, samples 10 may be deposited, in whole or in portion, on drum 100 using fiber 12 for dispensing the droplets onto the drum, whereupon fiber 12 may be removed.

Ribbon Transport

Figure 11A:
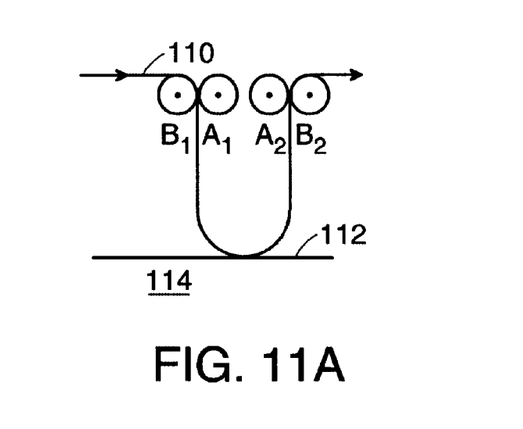
FIG. 11A is a side view in cross section of a liquid take-up mechanism employing ribbon or tape in accordance with an alternate embodiment of the present invention.
Figure 11B:
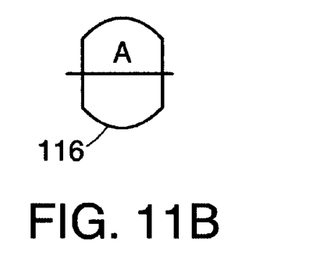
FIGS. 11B–11C show cross-sections of pulleys employed to impart curvature to the ribbon or tape of FIG. 11A.
Figure 11C:
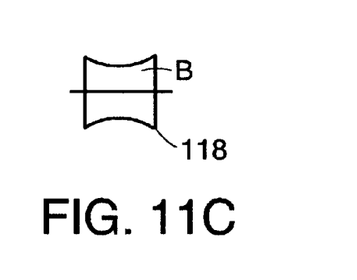

Referring now to FIGS. 11A–C, an alternate embodiment of the invention employs a flexible transport member for transportation of droplets where the flexible transport member is a tape or ribbon 110, as shown in cross-section in FIG. 11A. Tape 110 may be glass, quartz, metal, or various other materials. Amorphous metal (metallic glass) ribbon is preferred since it can sustain tight radii of bending and additionally has a very high tensile strength. These properties are advantage for high-rate sampling, using a loop feed mechanism having pulleys $A_1$, $B_1$, $A_2$, and $B_2$ as shown. As described with reference to FIG. 2A, flexible member 110 is brought into contact with surface 112 of liquid 114 and droplets adhere to the flexible member. In certain embodiments of the invention, it is desirable to impart a curvature to ribbon 110. This is achieved by providing respectively convex and concave curved circumferential surfaces 116 and 118 shown in FIGS. 11B and 11C, where pulleys A and B are shown in cross-section. The concave surface 118 may also serve as a recess for straddling liquid droplets borne by the flexible member.

Figure 12:
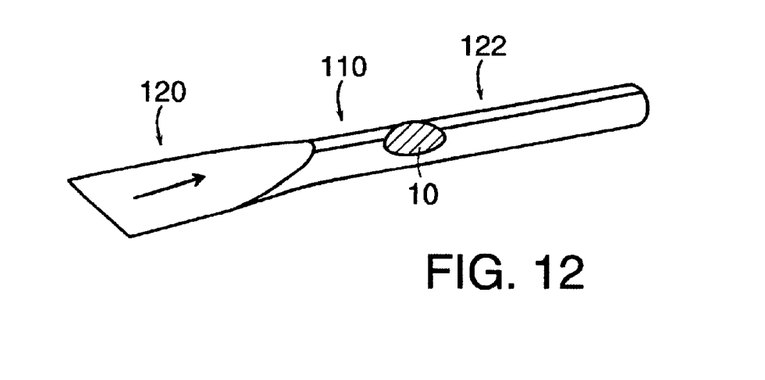
FIG. 12 is a perspective view of a ribbon employed in curled and flattened configurations for transport of microdroplets in accordance with embodiments of the invention.

Alternatively, as shown in FIG. 12, ribbon 110 may be fully curled in its entirety or in segments, such as to have flat segments 120 and fully curled segments 122. Full curling forms a cylinder which may be employed advantageously to encapsulate liquid droplet 10, thereby minimizing or eliminating evaporation of material from droplet 10 during any latency period required in processing the droplet. Ribbon 110 may subsequently be uncurled to provide ready access to liquid droplet 10.

The described embodiments of the invention are intended to be merely exemplary and numerous variations and modifications will be apparent to those skilled in the art. All such variations and modifications are intended to be within the scope of the present invention as defined in the appended claims.

I claim:

1. An apparatus for transporting at least one isolated droplet of a liquid having a surface tension, the droplet having a volume less than one microliter, the apparatus comprising:
   a. a reservoir for containing a quantity of the liquid;
   b. a flexible member characterized by a linear dimension and movable to a specified extent along the linear dimension of the member, the flexible member disposed for receiving the at least one isolated droplet of the liquid from the reservoir, the at least one isolated droplet of the liquid adhering to the flexible member by virtue of the surface tension of the liquid; and c. an impeller for urging the flexible member in at least one direction, the impeller comprising at least one pulley having a circumferential recess for straddling the at least one droplet during motion of the flexible member.

2. An apparatus according to claim 1, wherein the flexible member is a fiber.

3. An apparatus according to claim 1, wherein the flexible member has a characteristic cross-sectional dimension smaller than 100 micrometers.

4. An apparatus according to claim 1, wherein the flexible member is a ribbon.

5. An apparatus according to claim 1, wherein a portion up to the whole of the flexible member is formed at least temporarily into an enclosure for encapsulating at least one droplet of the liquid.

6. An apparatus according to claim 1, wherein the flexible member is composed of an amorphous material.

7. An apparatus according to claim 6, wherein the amorphous material is glass.

8. An apparatus according to claim 6, wherein the amorphous material is metal.

9. An apparatus according to claim 1, further comprising a mounting arrangement permitting bending of the flexible member while in motion.

10. An apparatus for transporting at least one isolated droplet of a liquid having a surface tension, the droplet having a volume less than one microliter, the apparatus comprising:

a. a flexible member characterized by a linear dimension and movable to a specified extent along the linear dimension of the member, the flexible member disposed for receiving the at least one isolated droplet of the liquid, the at least one isolated droplet of the liquid adhering to the flexible member by virtue of the surface tension of the liquid; and b. an impeller for urging the flexible member in at least one direction, the impeller comprising at least one pulley having a circumferential recess for straddling the at least one droplet during motion of the flexible member.

* * * * *